United States Patent [19]

Schmedemann

[11] Patent Number: 4,615,042
[45] Date of Patent: Sep. 30, 1986

[54] DISPLACEABLE X-RAY EXAMINATION TABLE

[75] Inventor: Walter Schmedemann, Tangstedt, Fed. Rep. of Germany

[73] Assignee: U.S. Philips Corporation, New York, N.Y.

[21] Appl. No.: 554,139

[22] Filed: Nov. 21, 1983

[30] Foreign Application Priority Data

Dec. 2, 1982 [DE] Fed. Rep. of Germany ....... 3244578

[51] Int. Cl.⁴ .......................... A61B 6/04; A61G 13/00
[52] U.S. Cl. ...................................... 378/209; 269/322
[58] Field of Search ............... 378/209, 177, 179, 195, 378/196; 269/322–326; 198/750, 856, 485

[56] References Cited

U.S. PATENT DOCUMENTS

| | | | |
|---|---|---|---|
| 2,252,336 | 8/1941 | Thomas | 198/856 |
| 3,029,957 | 4/1962 | Freeman et al. | 198/750 |
| 3,473,024 | 10/1969 | Feiertag | 378/209 |
| 4,164,656 | 8/1979 | Krasznai | 250/439 |

FOREIGN PATENT DOCUMENTS 688182  1/1940  Fed. Rep. of Germany .
1222624  8/1966  Fed. Rep. of Germany ...... 378/209

*Primary Examiner*—Craig E. Church
*Assistant Examiner*—Charles F. Wieland
*Attorney, Agent, or Firm*—Marc D. Schechter

[57] ABSTRACT

The invention improves the safety in the case of breakage of an endless chain whereby a part of an X-ray apparatus table top is supported and displaced by a chain. The chain is accommodated inside a rigid guide having a slot through which the chain is coupled to the table top. The guide is constructed so that the chain has only a limited freedom of movement on all sides.

3 Claims, 3 Drawing Figures

DISPLACEABLE X-RAY EXAMINATION TABLE

BACKGROUND OF THE INVENTION

The invention relates to displaceable X-ray examination table. The table top is displaceable by an endless chain which cooperates with a drivable sprocket.

A device of this kind is described in U.S. Pat. No. 3,473,024. The sprocket is driven by a motor, if necessary. When the motor of such an apparatus is stopped, the drivable sprocket is blocked in order to lock the table top in its position.

The chain of such a device is loaded by the forces acting on the table top. A broken chain could therefore endanger a patient resting on the table. In order to avoid the danger imposed by such a break, there are government regulations which effectively require a twelve-fold static protection if no additional protection is provided to prevent the table top from falling if the chain breaks. This means that the chain must be designed to bear twelve times the static load exerted by the table top during normal operation.

However, if such protection against falling is provided, the situation will be less critical if the chain breaks. In that case, the chain must be designed to bear merely for four times the highest load.

SUMMARY OF THE INVENTION

It is an object of the invention to provide a chain-driven table top which can move only slightly if the chain breaks.

According to the invention, the chain is accommodated inside a rigid guide which is fixed, in the displacement direction, relative to the X-ray apparatus. The guide is constructed so that the chain has only a limited freedom of movement on all sides. The guide is provided with a slot through which the chain is coupled to the table top.

The rigid guide thus encloses the chain on all sides, so that the chain can move only a little in the lateral directions; i.e. in the directions perpendicular to the chain. Should the chain break, (such a break usually takes place at an area where the chain is subjected to tensile load), the table top will compress the other part of the chain. Since the chain cannot yield in the lateral direction because the chain is blocked by the guide, the chain takes up the force and retains the apparatus part in substantially the same position in which it was situated prior to the breakage of the chain.

The guide may in principle consist of several portions which separately enclose the drivable sprocket and also an idler sprocket for guiding the chain and the chain portions which are situated between the sprockets. In a further preferred embodiment according to the invention, however, the guide is constructed as a rail having a hollow profile with recesses for the sprockets and ducts for the chains.

According to the invention the rail serves two purposes: on the one hand, the rail guides the table top, and on the other hand the rail prevents, in conjunction with the chain, the tabletop from falling.

DESCRIPTION OF THE PREFERRED EMBODIMENTS

Figure 1:
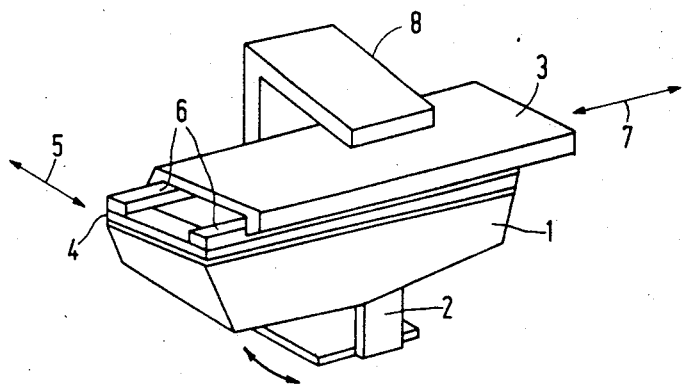
FIG. 1 is a perspective view of an X-ray examination apparatus in which the invention can be used.

FIG. 1 shows an X-ray apparatus having a frame 1 which is arranged so as to be tiltable about a horizontal axis in a base 2. The frame supports a carriage 4 which is displaceable parallel to the tilt axis (i.e. in the direction of the double arrow 5). Carriage 4 comprises two parallel guide rails 6 which extend perpendicularly to the tilt axis. Guide rails 6 serve to a guide a table top 3 in its longitudinal direction (i.e. in the direction of the double arrow 7). The X-ray apparatus also comprises an imaging section 8.

The table top 3 is displaced by a chain (not shown in FIG. 1) on which a motor acts via a sprocket (not shown in FIG. 1). When the motor is switched off, the sprocket driven thereby is blocked (for example by using a self-braking drive and to form a brake motor) so that the table top remains in its position. The table top 3 remains in its position even when it is perpendicular and loaded by a patient, for example via a foot rest (not shown). The X-ray apparatus described thus far is known.

Figure 2:
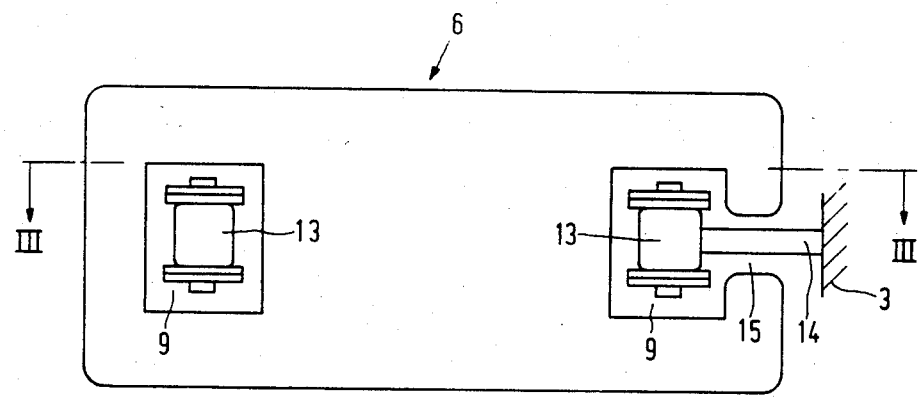
FIG. 2 is a sectional view, taken in a direction perpendicular to the chain, of a guide which is constructed as a rail having a hollow profile.
Figure 3:
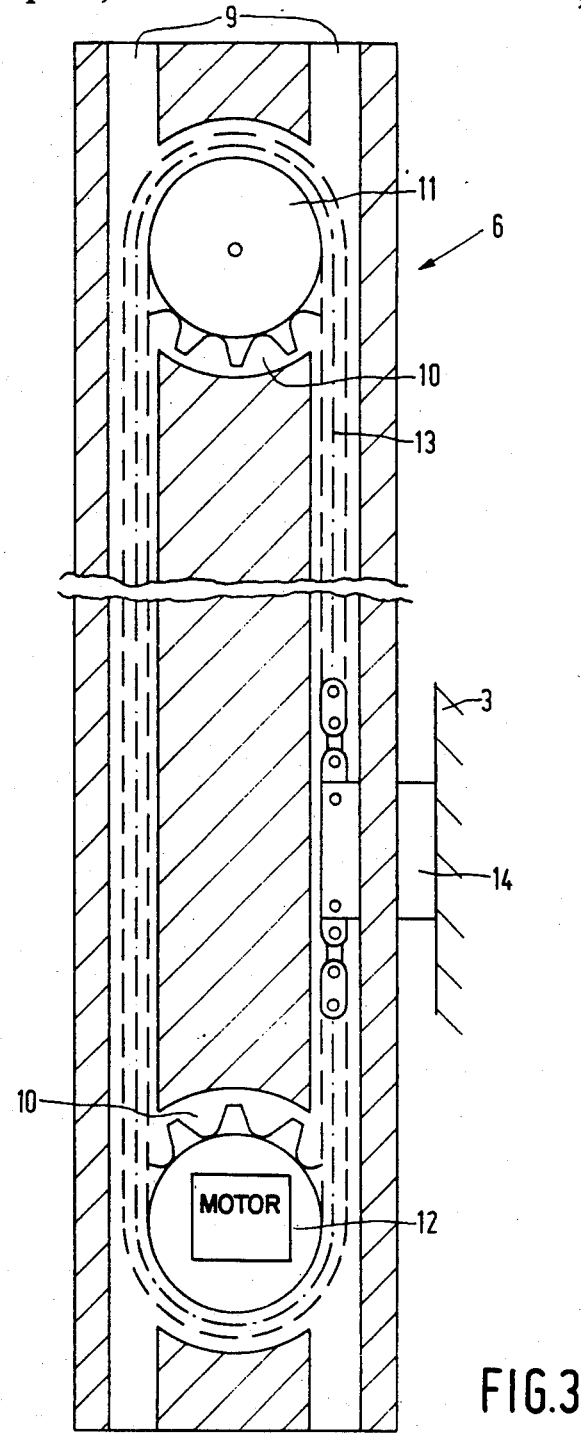
FIG. 3 is a sectional view of a portion of the guide of FIG. 2 in a direction parallel to the plane of the chain.

FIGS. 2 and 3 are cross-sectional views of a guide rail 6 taken in a direction perpendicular to the table top (FIG. 2) and in a plane parallel to the table top (FIG. 3). The guide rail 6 has a hollow profile with two ducts 9 of rectangular cross-section which extend in the longitudinal direction of the rail. Near the ends of the rail there are provided two cylindrical recesses 10 in which sprockets 11 and 12, respectively, are accommodated. The sprocket 12 is coupled to a self-braking drive motor 20 (schematically shown in FIG. 3).

Around the sprockets there is guided a roller chain 13, for example in accordance with DIN 8187, which travels in the ducts 9 of rail 6. The drawing shows only a few of the links of the chain 13. To the roller chain 13 there is connected a coupling device 14. Coupling device 14 projects through a slot 15, extending in the longitudinal direction of the rail, and is connected to one side of the table top 3.

The dimensions of the slot 15 are smaller than the dimensions of a link of the chain 13, so that the chain cannot pass through the slot 15 in the lateral direction. As appears in FIGS. 2 and 3, the dimensions of the recesses 10 and the ducts 9 are adapted to the dimensions of the sprockets 11 and 12 and the chain 13 so that at all areas the chain 13 travels at a small distance (for example, 1 mm) from the inner walls of the guide rail 6 enclosing the chain.

When the X-ray apparatus has been tilted to a vertical position so that the guide rail 6 occupies a position in which the drivable sprocket 12 is situated at the lower end of the rail 6, the weight of the table top 3 (and of the patient accommodated thereon) acts on the chain 13 via the coupling device 14. The portion of chain 13 which is situated between the coupling device 14 upper guide sprocket 11 and the portion of chain 13 which directly links the two sprockets are thus subjected to a tensile load. The remaining portion (between the coupling device 14 and the drivable sprocket 12) is loaded only in correspondence with the chain bias.

Should the tensile loaded portion of the chain break, it will be relieved while the remainder of the chain is subjected to a compressive load. Due to the close guiding of the chain in the duct 9 and the recess 10, the chain cannot escape this load in the lateral direction (also in the direction perpendicular to the plane of drawing of FIG. 3). Because, as described with reference to FIG. 1, the drivable sprocket 12 is either blocked or can rotate only at the angular velocity determined by the activated motor, the chain portion present between the coupling device 14 and the drivable sprocket 12 is subjected to a compressive load, so that the table top 3 cannot fall down but moves only little as the motor slowly turns.

Consequently, if the chain 13 breaks, the table top cannot fall down. Therefore, the chain 13 need be designed to bear only four times the highest static load, so that it may be comparatively thin.

The second guide rail 6 can be provided as a mirror image of the first rail, so that the slots in the two rails are each situated remote from the other rail. The sprockets should then be driven with the same number of revolutions, but in opposite directions. The chain 13 need not be rigidly connected to the table top 3, but may be coupled thereto by way of a toothed rack which is rigidly connected to the table top and whose teeth engage the chain.

I claim:

1. An X-ray examination table having a displaceable table top, said examination table comprising:
    a self-braking motor;
    a drive sprocket drivable by the motor;
    an endless chain engaged by the drive sprocket, said chain movable along an endless curved path around the sprocket; and
    a rigid guide having a duct therein, the chain being arranged in the duct in the guide, said guide having a slot therein through which the chain is coupled to the table top, said duct having dimensions such that the chain cannot move substantially transverse to the endless curved path.

2. An X-ray examination apparatus as claimed in claim 1, characterized in that the guide is a rail, and the duct in the guide has a recess for the drive sprocket and a recess for an idler sprocket, the chain movable along the endless curved path around the sprockets.

3. An X-ray examination table having a displaceable table top, said examination table comprising:
    a self-braking motor;
    a drive sprocket drivable by the motor;
    an idler sprocket;
    an endless chain engaged by the drive sprocket and by the idler sprocket, said chain movable along an endless curved path around the two sprockets, said path being the shortest path around the two sprockets; and
    a rigid guide having a duct therein, the chain being arranged in the duct in the guide, said guide having a slot therein through which the chain is coupled to the table top, said duct having dimensions such that the chain cannot move substantially transverse to the endless curved path, said duct having a recess for the drive sprocket and another recess for the idler sprocket.

* * * * *